United States Patent
Cadell et al.

(12) 
(10) Patent No.: US 6,522,398 B2
(45) Date of Patent: *Feb. 18, 2003

(54) APPARATUS FOR MEASURING HEMATOCRIT

(75) Inventors: Theodore E. Cadell, Conestogo (CA); James Samsoondar, Cambridge (CA)

(73) Assignee: CME Telemetrix Inc., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/732,211

(22) Filed: Dec. 8, 2000

(65) Prior Publication Data

US 2001/0004285 A1 Jun. 21, 2001

Related U.S. Application Data

(62) Division of application No. 09/068,835, filed on Feb. 8, 1999, now Pat. No. 6,195,158.

(51) Int. Cl.$^7$ ................... G01N 21/47; G01N 21/59
(52) U.S. Cl. .................................. 356/39; 356/440
(58) Field of Search ................. 356/39, 246, 440; 600/322; 422/82.05, 82.09; 436/164, 165; 73/61.4, 61.65, 61.66

(56) References Cited

U.S. PATENT DOCUMENTS

4,125,327 A * 11/1978 Margolis .................... 356/39
4,683,579 A *  7/1987 Wardlaw .................... 356/39

FOREIGN PATENT DOCUMENTS

EP             479622 A1 * 10/1991

* cited by examiner

*Primary Examiner*—Zandra Smith
(74) *Attorney, Agent, or Firm*—Katten Muchin Zavis Rosenman

(57) ABSTRACT

A method and apparatus for use in respect of samples which are assessed for quality prior to testing in a clinical analyzer. The method and apparatus identify parameters such as gel level and height of fluid above the gel in blood samples, where appropriate, for the purposes of positioning the specimen for determination of interferents. Such interferents include hemoglobin (Hb), total bilirubin and lipids. These interferents are determined by measurement of absorption of different wavelengths of light in serum or plasma, or other speciments, which are then compared with values obtained through calibration using reference measurements for the respective interferents in serum or plasma or other type of specimen. Determination of temperature of the specimen, as well as specimen type, for example whether the specimen is urine or plasma or serum, may also be carried out.

4 Claims, 2 Drawing Sheets

APPARATUS FOR MEASURING HEMATOCRIT

RELATED APPLICATION INFORMATION

This is a divisional application of U.S. patent application Ser. No. 09/068,835 filed Feb. 8, 1999, now U.S. Pat. No. 6,195,158.

TECHNICAL FIELD

This invention relates to spectrophotometry and the spectrophotometric analysis of blood samples. In particular, this invention relates to a method and apparatus for providing a rapid pre-test determination of interferent concentration, specimen type and physical properties of a blood sample for a blood analyzer by measurement of absorbance or reflectance.

BACKGROUND ART

Clinical laboratory tests are routinely performed on the serum or plasma of whole blood. In a routine assay, red blood cells are separated from plasma by centrifugation, or red blood cells and various plasma proteins are separated from serum by dotting prior to centrifugation.

Haemoglobin (Hb), bilirubin (Bili) and light-scattering substances like lipid particles are typical substances which will interfere with, and affect spectrophotometric and other blood analytical measurements. Such substances are referred to as interferents.

Many tests conducted on plasma or serum samples employ a series of reactions which terminate after the generation of chromophores which facilitate detection by spectrophotometric measurements at one or two wavelengths. Measurement of interfering substances prior to conducting such tests is important in providing meaningful and accurate test results. In fact if a sample is sufficiently contaminated with interferents, tests are normally not conducted as the results will not be reliable.

In analytical laboratories bar codes are increasingly being used to identify samples, and such laboratories routinely analyze a variety of biologic fluids, for example, the most common being blood and urine.

Specimen integrity directly affects the accuracy of test results. Numerous factors can compromise specimen integrity such as, having the right sample, e.g., blood rather than urine; in the case of a blood sample, whether it is serum or plasma; the presence of interferents in a plasma or serum sample; the volume of the sample; the sample temperature; and the location of the upper surface of a gel barrier, which is also referred to herein as the gel level, in a blood sample, where the gel is an inert material used to separate serum or plasma from clotted or packed blood bells, respectively. Finally, it is critical that the sample tested be properly matched to the results of any assessments on the sample.

Current methods used for quality assurance and specimen integrity rely principally on visual inspection of the specimen with or without comparison to a reference chart, depending upon which variable is being assessed. Visual inspection of samples is sometimes employed on a retrospective basis where there is disagreement between test results and clinical status of the patient in order to help explain such discrepancies.

A sample of plasma or serum is normally transferred from the original tube to a secondary tube. These secondary tubes may be amber coloured to protect photo sensitive constituents. Amber colouring makes visual inspection virtually impossible. On occasion, labels cover portions of the tube further restricting a full visual examination. Further, it is sometimes difficult to distinguish between urine and plasma or serum samples, even in transparent tubes.

Pre-test screening of specimens by visual inspection is semi-quantitative at best, and highly subjective and may not provide the quality assurance required.

Furthermore, visual inspection of specimens is a time consuming, rate limiting process. Consequently, state-of-the-art blood analyzers in fully and semi-automated laboratories do not employ visual inspection of specimens. However, other methods such as direct sampling are not rapid enough or cost effective. In order to obtain a measurement of the sample of the plasma or serum, specimen tubes must be uncapped, a direct sample of the specimen taken and diluted prior to measurement.

SUMMARY OF INVENTION

The disadvantages of the prior art may be overcome by providing a rapid and accurate method and apparatus for monitoring blood specimens before samples are presented for analysis.

In one aspect of the invention, the bar code on the specimen tube is read to identify the specimen, as well as the bar code reading, determination of the gel level of the specimen and the height of fluid above the gel provide the basis for positioning the specimen container so that spectral data can be obtained. The spectral data is used in a novel way to determine if the specimen which is presented for analysis contains interferents and if so, to what extent; to determine specimen type, for example if it is urine or plasma or serum; and to determine the temperature of the specimen.

In another aspect of the invention, there is provided an apparatus which incorporates: A. a device to read any bar code present on a specimen container and thereby identify and provide information with respect to positioning the specimen; B. a device to determine the location of the upper surface of a gel barrier of the specimen and the height of fluid above the gel; and C. A spectrophotometric device to irradiate and measure radiation from the specimen so as to determine if the specimen which is presented for analysis contains interferents and if so, to what extent; to determine specimen type; and to determine the temperature of the specimen. This apparatus is capable of these determinations where the sample tube containing the specimen has a sample identification label on the exterior surface.

In a further aspect of the invention, there is provided a method for the following: to read any bar code present on specimen container and thereby identify and provide information with respect to positioning the specimen; to determine the location of the upper surface of a gel barrier of the specimen and the height of fluid above the gel; to determine if the specimen which is presented for analysis contains interferents and if so, to what extent; to determine specimen type; and to determine the temperature of the specimen. The method of this invention allows for these determinations where the sample tube containing the specimen has a sample identification label on the exterior surface.

In yet another aspect of the invention, there is provided an apparatus and a method for the determinations described herein where the radiation from the spectrophotometer, or other appropriate source, is transmitted through the label, container and specimen.

In one embodiment, the bar code reading as well as the gel level and height of fluid above the gel are first determined. This determination provides information essential for proper positioning of the sample for the following determinations. The concentration of interferents such as hemoglobin (Hb), total bilirubin (calibrated for unconjugated bilirubin, conjugated bilirubin, delta bilirubin, the sum of results for these three gives total bilirubin) and lipids are determined by measurement of absorption of different wavelengths of light in serum or plasma specimens which are then compared with values obtained through calibration using reference measurements for the respective interferents in serum or plasma specimens. This is true also for determination of temperature of the sample. A determination of specimen type, for example whether the specimen is urine or plasma or serum, is also made. This determination is made by recordal of spectral data for different samples then through statistical analysis, the spectra are classified according to sample type. In addition a bar code reading is carried out either simultaneously, before or after the determination of the other parameters. To those skilled in the art, it is clear that although certain sequences of determinations are outlined here, any combination or sequence of combinations is within the scope of this invention.

In another embodiment, the bar code reading as well as the gel level and height of fluid above the gel are first determined. This determination provides information essential for proper positioning of the sample for the following determinations. The concentration of interferents such as hemoglobin (Hb), total bilirubin (calibrated for unconjugated bilirubin, conjugated bilirubin, and delta bilirubin, the sum of results for these three gives total bilirubin) and lipids are determined by measurement of reflectance of different wavelengths of light in serum or plasma specimens which are then compared with values obtained through calibration using reference measurements for the respective interferents in serum of plasma specimens. This is true also for determination of temperature of the sample. A determination of specimen type, for example whether the specimen is urine or plasma or serum, is also made. This determination is made by recordal of spectral data for different samples then through statistical analysis, the spectra are classified according to sample type. In addition a bar code reading is carried out either simultaneously, before or after the determination of the other parameters. To those skilled in the art, it is clear that although certain sequences of determinations are outlined here, any combination or sequence of combinations is within the scope of this invention.

DESCRIPTION OF PREFERRED EMBODIMENTS

In operation, the apparatus first conducts a determination of the bar code and its position on the tube, and, based on the latter determination the tube is presented to the specimen holder 2 in a position so that the bar code does not interfere with the measurement process.

Figure 1:
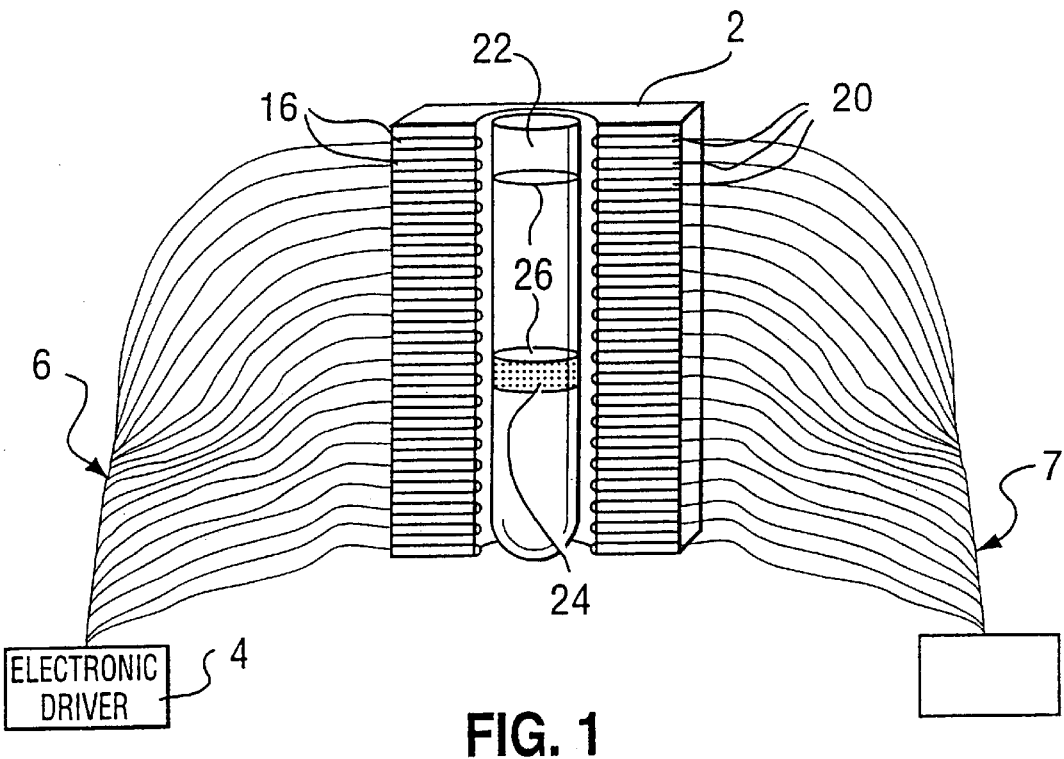
FIG. 1 is a longitudinal cross-section of a sample holder adapted for use with LED and radiation source.

With respect to measuring gel level and height of fluid 26 above the gel 24, the specimen is placed in a specimen holder 2 of FIG. 1, which will also contain a linear array of LEDs 16 on one side of the tube, and a corresponding array of silicon detectors 20 on the opposite side of the tube. The LEDs 16 are coupled by electrical connections 6 to an electronic driver 4. The detectors 20 are coupled by electrical connections 7 to a microprocessor (not shown) which analyzes output. The number of LEDs and detectors will depend on the length of the tube, e.g., for a commonly used tube of length 10 cm, 22 LEDs and 20 detectors arranged 5 mm apart will be necessary to accommodate from a completely filled tube to an empty tube. In operation the first detector at the top of the column monitors as the three LED's opposite are flashed in succession: one which is directly opposite, one 5 mm above, and one 5 mm below. The measured distance between the LEDs and the detectors is used to determine tube diameter. This measurement is performed electronically, mechanically or optically, or in any combination of these. In a preferred embodiment this measurement is performed by a combination of mechanical and electronic operations. The fluid volume is calculated from the measured tube diameter and the measured height of fluid above the gel barrier.

Alternatively, with respect to measuring gel level and height of fluid, a diode laser provides the radiation source wherein the source is focused through a series of lenses 30 to spread the radiation 32 across the length of the sample tube. The light being transmitted through the sample tube is passed through a further series of lenses 34 and directed onto a PDA sensor 36. Again, through this apparatus the tube is analyzed in 1 mm increments and the results are correlated to liquid height 26 and gel level 24. It is readily apparent that either approach also allows for the determination of the hematocrit of any blood sample. This is achieved by centrifuging a whole blood sample in a container into two phases, one being the blood cells and the other being serum or plasma. The container is then scanned by the present invention and the length of the container that each of the phases occupies is thereby determined. With this data the ratio of the length amounts of the cellular phase and of the serum or plasma phase is converted to hematocrit value.

Based upon the results from the above determinations, the relative positions of the tube and the fibre optics can be adjusted so as to optimize the position of the fluid compartment for subsequent determinations. Consequently, there is space between the walls of the sample holder 2 and the fibre optics 10 and 14 to allow for such adjustments.

Figure 2:
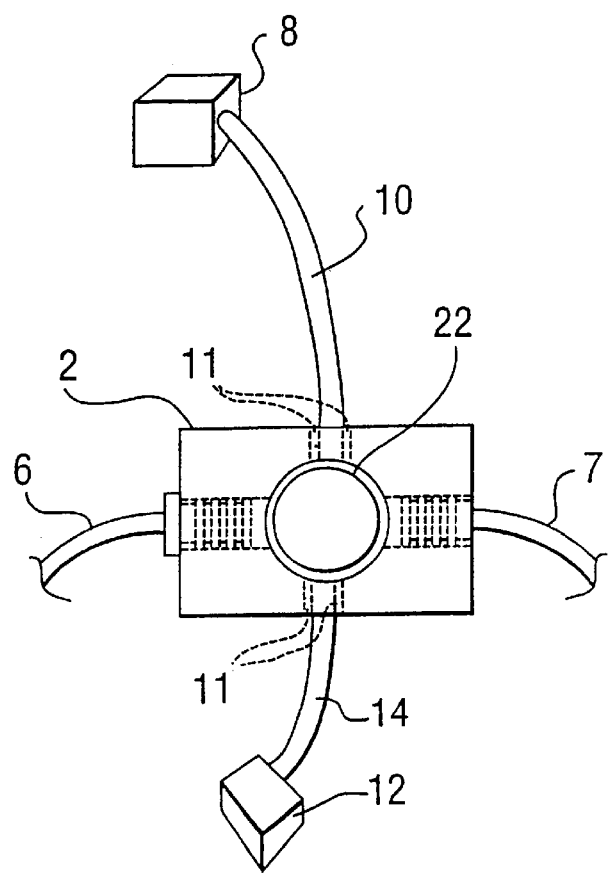
FIG. 2 is a top view of the complete sample holder of FIG. 1.
Figure 3:
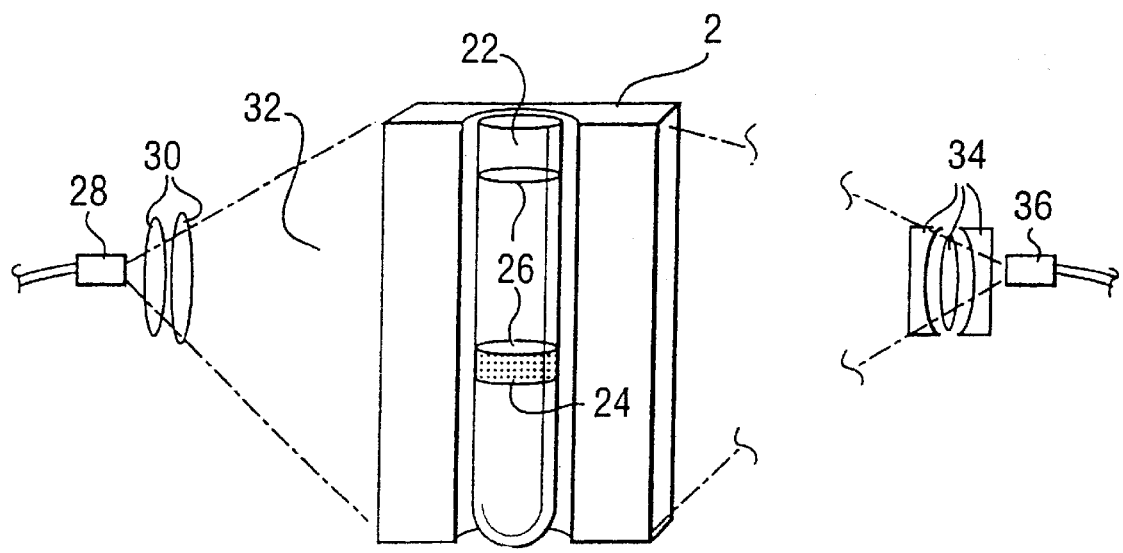
FIG. 3 is a longitudinal cross-section of a sample holder adapted for use with a laser and radiation source.
Figure 4:
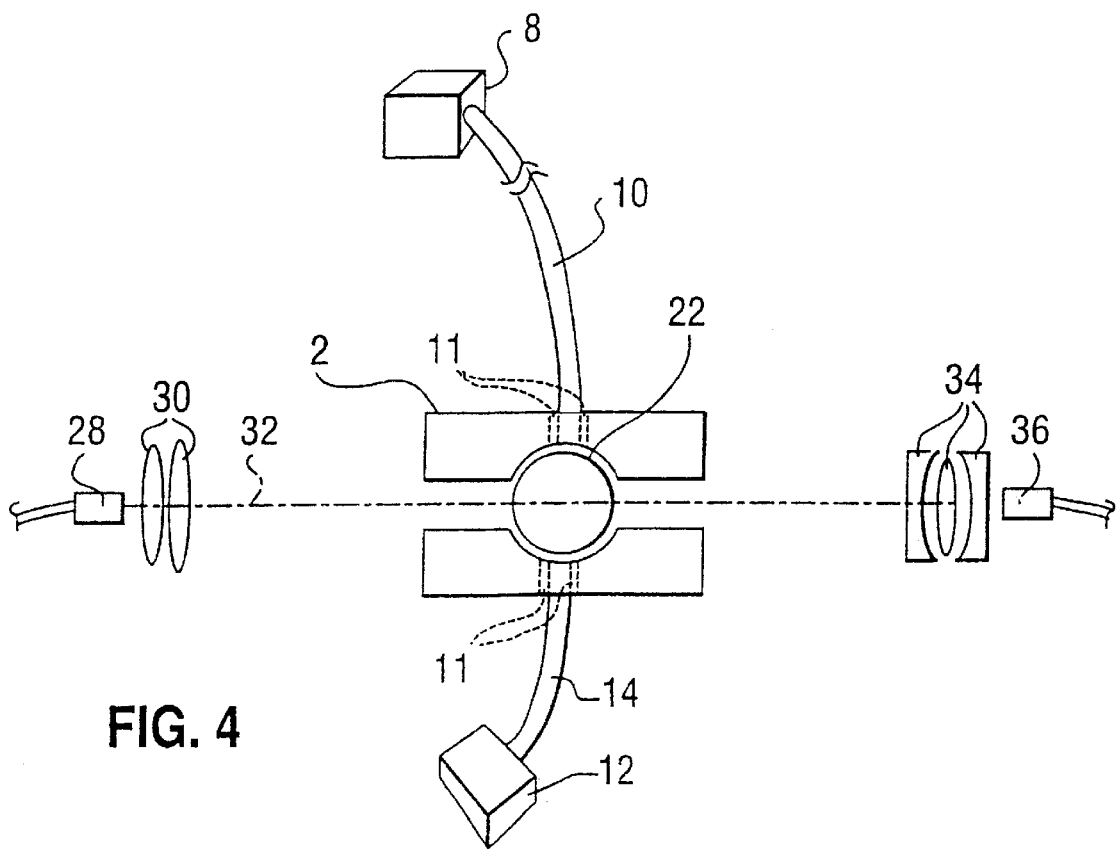
FIG. 4 is a top view of the complete sample holder of FIG. 3.

With respect to determination of sample type, temperature, as well as for measurement of interferents, reference is made to FIG. 2. The sample 22 is placed into a specimen holder 2 (see FIG. 1 for longitudinal view) which is located in a housing (not shown). A radiation source 8, capable of emitting radiation in a range from about 400 nm to 2,500 nm, is optically connected by fibre optics 10 to the sample. In operation where absorbance is measured the light source is directed through the sample, and the transmitted radiation is detected by a sensor 12, which is a photo diode array (PDA), that is located opposite the source. In operation where reflectance is measured, the detectors are proximate to the emission source (not shown). In both cases the detector is optically connected by fibre optics 14, or any other suitable means. In this apparatus the radiation source is split so that there is a reference beam which bypasses the sample. The apparatus also contains a means for correlating a sensor response, from the sample path relative to a sensor response from the reference path, to a quantity of a known substance in said sample. The housing has a cavity for receiving a sample and a lid for selectively opening and closing the cavity. The radiation source is for emitting a beam of radiation, and the sensor is responsive to receipt of radiation.

While the invention has been particularly shown and described with reference to certain embodiments, it will be understood by those skilled in the art that various other changes in form and detail may be made without departing from the spirit and scope of the invention.

We claim:

1. An apparatus for determining the hematocrit of a blood sample said apparatus comprising:
   a) means for holding a specimen container wherein said means and said container have a longitudinal axis;
   b) a radiation source disposed to direct radiation at said specimen and a radiation detector disposed to allow collection of transmitted or reflected radiation from said specimen, said radiation source comprising a linear array of LEDs disposed along one side of said axis of said container and said radiation detector comprising a corresponding array of silicon detectors on the opposite side of said container to collect transmitted radiation;
   c) electrical means to couple said radiation source to an electronic driver; and
   d) electrical means to couple said radiation detector to a computing means which analyzes output from said detector for determination of hematocrit of said sample.

2. The apparatus of claim 1 further comprising one or more lenses to focus said radiation from said radiation source to spread said radiation across said axis of said container, and further wherein said Apparatus contains one or more further lenses which collect transmitted or reflected radiation from said specimen and direct it to a spectrophotometric radiation detector.

3. The apparatus of claim 1 or 2 wherein said specimen container contains a sample identification label on the exterior surface of said container.

4. The apparatus of claim 1 or 2 wherein said radiation is transmitted through a label, a container and a sample.

* * * * *